United States Patent [19]

Laucournet

[11] Patent Number: 5,742,398
[45] Date of Patent: Apr. 21, 1998

[54] DEVICE FOR THE AUTOMATIC DETECTION AND INSPECTION OF DEFECTS ON A RUNNING WEB, SUCH AS A TEXTILE FABRIC

[75] Inventor: Gilles Laucournet, St. Maurice de Gourdans, France

[73] Assignee: ICBT Macotex, France

[21] Appl. No.: 731,587

[22] Filed: Oct. 16, 1996

[30] Foreign Application Priority Data

Oct. 16, 1995 [FR] France .................. 95 12318

[51] Int. Cl.[6] .................................. G01N 21/89
[52] U.S. Cl. .............. 356/429; 250/559.46; 356/430
[58] Field of Search ........................ 356/429, 430, 356/23; 250/559.45, 559.46

[56] References Cited

U.S. PATENT DOCUMENTS 4,714,340  12/1987  Stillwagon .................. 356/23
5,243,402  9/1993  Weber et al. ................ 356/429

FOREIGN PATENT DOCUMENTS

| 0311014 | 4/1989 | European Pat. Off. . |
| 3904897 | 8/1989 | Germany . |
| 4031633 | 4/1992 | Germany . |
| 575592 | 5/1976 | Switzerland . |
| 2224831 | 5/1990 | United Kingdom . |

*Primary Examiner*—Vincent P. McGraw
*Attorney, Agent, or Firm*—Wall Marjama & Bilinski

[57] ABSTRACT

Apparatus for detecting defects in a web of textile material as it is being drawn through an inspection zone. A header is arranged to project a line of light on the running web and a reflected light image from the web is sensed and analyzed for defects. The header includes a fiber bundle for producing a line of light and an optical element for collimating the light upon the web as it passes through the inspection zone.

10 Claims, 5 Drawing Sheets

DEVICE FOR THE AUTOMATIC DETECTION AND INSPECTION OF DEFECTS ON A RUNNING WEB, SUCH AS A TEXTILE FABRIC

FIELD OF THE INVENTION

The invention relates to a device for the automatic detection and inspection of defects on a running web, such as a textile fabric. It therefore relates to the field of quality control of a web of material, more particularly of textile fabric. It is therefore an examination device using an artificial vision system.

PRIOR ART

In a known manner, after manufacture of a textile fabric, especially a cloth, an additional operation is generally carried out, called "cloth examining", just before packaging. This operation consists in making the fabric run past an operator who detects any manufacturing or appearance defects present on the running web. In physical terms, this operation is performed on a machine called a "cloth examining machine" which comprises means for unreeling the cloth initially in the form of a beam, means for tensioning said cloth, a cloth examining table and a unit for reeling up the examined fabric.

In general, cloth examining tables are inclined so as to present the cloth in front of the operator's eyes. This cloth examining table includes means of illumination from above and/or from below the running cloth to be examined.

Unfortunately, the allowed run speeds for accurate inspections are limited to twenty meters per minute at most. Moreover, visual inspection requires the permanent presence of an operator, of whom it is known that he is able to detect only half the defects present and whose attention, because of fatigue, fluctuates over the day.

In the document U.S. Pat. No. 4,619,527, it was proposed to make use of automatic defect detection based on the acquisition of a digital image of the cloth and on the processing of this image. This acquisition uses optoelectrical sensors which convert the light transmitted by the yarns in the cloth into a logic signal which is then stored in memory. This digital image obtained is then processed in order to detect any defects in the cloth. The principle used consists in measuring the difference in the luminosity values which are obtained by measuring luminosity averages. Unfortunately, this type of cloth examining machine, especially because of the processing unit, is very sensitive to the differences in light variations. Moreover, the complex processing carried out on the images does not allow the run speed of the cloth to be appreciably increased.

The document U.S. Pat. No. 5,243,402 describes an apparatus allowing inspection of a running web in which the illumination of this web is localized into a straight light line. This light line is obtained from a conventional light source associated with a bundle of optical fibers, one end of which is located in proximity to the light source while the other end is opened out into the form of a comb, forming a header. This header is positioned in proximity to a concave cylindrical mirror intended to focus the light emitted by the fiber-optic header onto the running web into the light line. The fraction of light in the light line which has passed through the running web is then picked up by an acquisition and processing system. This installation requires the use of a cylindrical mirror which proves to be particularly bulky and expensive. Furthermore, on account of the positioning of the ends of the optical fibers with respect to the mirror, in order to obtain a fine light line, it is necessary to position the web to be inspected very accurately with respect to the characteristic optical points. This system is consequently relatively sensitive to variations in the placing of the web to be observed. It follows that the operations of placing the web to be observed require great meticulousness often incompatible with speed of execution.

The problem which the invention proposes to solve is to provide a cloth examining machine operating automatically, whose illumination of the area on which the inspection takes place is sufficiently powerful and adjustable in order to allow effective detection of the defects, without having to make use of the operator, whose presence is nevertheless useful in order to qualify the defect detected.

DESCRIPTION OF THE INVENTION

The invention relates to a device for the automatic detection and inspection of defects on a running web, such as a textile fabric, comprising:

- a means for driving, from a wound package, the web to be inspected;
- elements for deflecting the running web and elements for tensioning it;
- an inclined plane for observation of the web running flat over this plane;
- a means for illuminating, over the entire width, a portion of the web running over the inclined plane, said means being formed by a header consisting of a plurality of optical fibers which are arranged side by side and supplied by at least one light source which is intended to form, on the running web, an individual line of reflected and stabilized light;
- a means for acquiring the images of the running web, consisting of at least one camera carrying a linear array of photosensitive sensors on which the image of the individual line of light is formed;
- means for processing these images, consisting of an electronic processing system intended to generate defect signals depending on the images transmitted by the cameras;
- a means for winding on the inspected web into the form of a wound package;
- means for controlling the drive means and the winding-on means when a defect signal is detected;
- a means for storing in memory the position on the web of the defects detected.

This device is one wherein the header is composed of a transparent cylindrical bar, the object focal point of which coincides with the end of the optical fibers so as to focus the emitted light onto the running web.

In other words, the invention consists in providing the fiber-optic header with a cylindrical bar acting optically as a convergent lens making it possible to focus into the form of a parallel beam the various light lines emanating from the fiber-optic header, by virtue of the positioning of the ends of the optical fibers at the object focal point of this lens. The system is consequently insensitive to the exact position of the running web with respect to the header. Put another way, it is possible for the header to be separated from the cloth by a markedly greater distance than that allowable in the prior art. This allows greater controllability and facilitates the operations of manually placing the cloth.

In order to solve the problem posed of tailoring the illumination according to the nature of the web to be treated, the inclination, direction and distance adjustment of the illumination header with respect to the cloth is controlled by the electronic system depending on the surface finish of the running web.

In order to solve the problem of powerful illumination concentrated on the area on which the inspection takes place, the light source consists of a stabilized halogen lamp associated with a heat-absorbing filter arranged at one end of a compact bundle of optical fibers, the other end of which is in the form of a straight header in which the individual fibers are arranged side by side. The illumination system uses optical fibers to form a straight strip of light from individual point light sources. Thus, the invention uses a plurality of bundles of optical fibers, one of the ends of each bundle assembling and concentrating all the optical fibers so that it picks up the light emitted by the light source, the other end of the bundle being opened out and separated in order to form a further straight partition of these optical fibers.

In order to enable the camera to be triggered when the web has run a length corresponding to the height of the image acquired by the camera, taking into account the optical reduction ratios of this camera, the coding pitch of the coder is less than the length of web whose image is obtained by the linear photosensitive sensor. In this manner, the triggering of the camera is slaved to the running of the web in such a way that the images taken successively by the camera allow the complete image of the running web to be reproduced.

Advantageously, the electronic central processing unit comprises image-acquisition electronic cards connected to the camera and to the coder, parallel-processing electronic cards connected to said acquisition cards, and electronic cards for communication with the means for controlling the device. Thus, parallel processing of the images received from the camera makes it possible to decrease the processing time substantially and thus to increase the rate of inspection, which may be doubled or even tripled.

In one advantageous form of the invention, the inclined inspection plane comprises a light-reflecting polished bar arranged on the wrong side of the running web, so as to coincide with the individual line of light. This bar is intended to reflect that part of the light which has passed through the running web via the holes or apertures made in the web.

In an improved form of the invention, the device includes a second means of illumination intended to illuminate that side of the cloth facing the inclined plane, in order to observe the cloth in transmitted light. Advantageously, the second means of illumination consists of a second header formed by a plurality of optical fibers.

In order to allow inspection of webs of very different types, especially with regard to their material and the contrast in the pattern and in the weave of which they are composed, the intensity of the light source can be adjusted depending on the type of web to be inspected.

Thus, the contrast of the web may be advantageously determined by virtue of the invention during a first acquisition operation allowing automatic calibration of the intensity of the light as a function of the quality of the cloth.

In this manner, the light power available in the illumination header is used to the maximum and the detection of defects is thus improved.

The manner in which the invention is realized and the advantages which stem therefrom will be very apparent from the following illustrative embodiment, supported by the appended figures.

MANNER OF REALIZING THE INVENTION

The invention relates to a device for monitoring the surface finish of a running web, which is most particularly advantageous when applied to the examining of textile fabric, such as a cloth, on machines generally called "cloth examining machines".

A cloth examining machine is composed of a circuit for running the cloth past an operator (A) as well as of a system of elements for monitoring and controlling the running movement.

Figure 1:
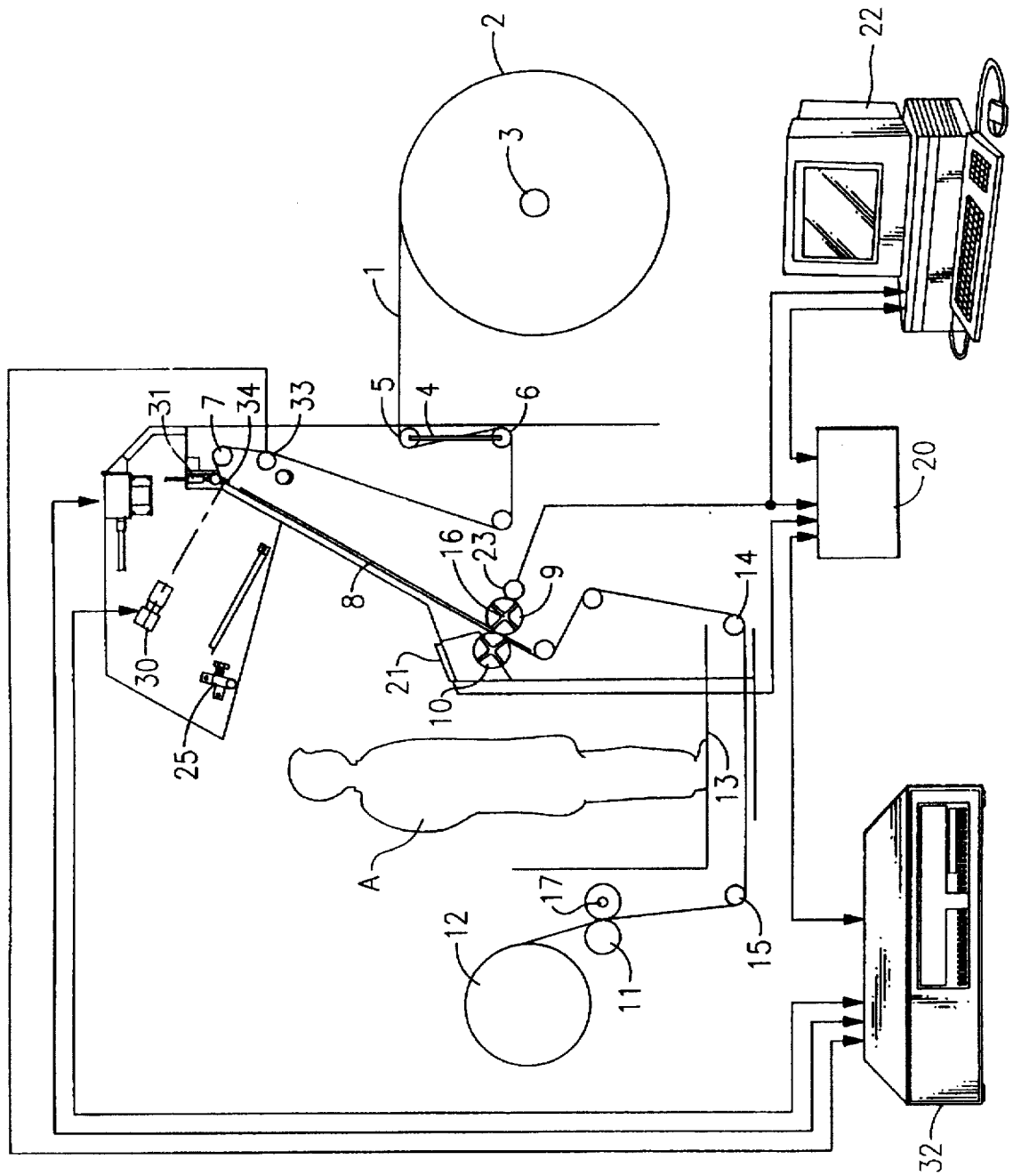
FIG. 1 is a general synoptical diagram of the entire cloth examining machine in accordance with the invention and of its main control elements.
Figure 2:
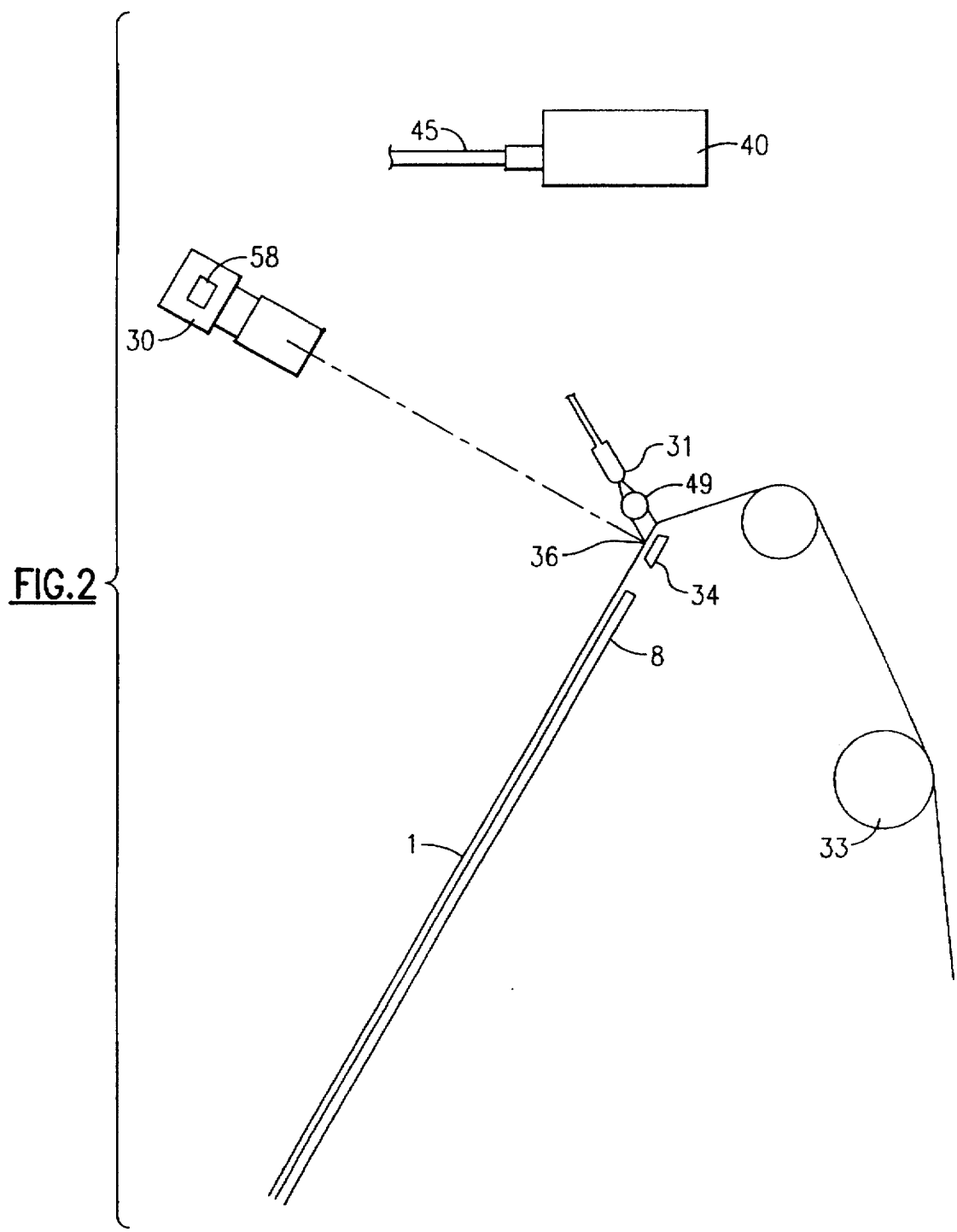
FIG. 2 is a detailed side view of the illumination area.

FIG. 1 illustrates a particular architecture of this improved cloth examining machine according to the invention.

The cloth (1) to be inspected is in the form of a beam (2), forming a large diameter roll, rotationally driven by known supply means (3). The unreeled cloth (1) passes through a dancer (4) formed from two coupled rollers (5, 6) which are intended to maintain it under sufficient tension. The cloth then encounters an upper deflection roller (7) after which it comes back down over the cloth examining table (8). This cloth examining table (8) is inclined rearward in order to allow optimum viewing by the operator (A).

The cloth (2) is made to run over the cloth examining table (8) by two drive rollers (9, 10) pressing together. Concomitantly, the cloth is conveyed to the reeling-up area by a set of rollers (11) allowing the cloth to be returned into the form of a beam (12). Of course, the speeds of the unreeling, running and reeling-up systems are coupled. In general, the rewinding takes place behind the operator so that the cloth passes under the floor on which the operator stands by means of a plurality of deflection rollers (14, 15).

The motors (3, 16 and 17), respectively associated with the beam unreeling system, with the running system (9, 10) and with the reeling-up system (11), are of the asynchronous type and are controlled by variable-speed drive units of known type. These undulators are managed by a programmable controller (20) which provides the synchronism between the various motors and provides the management of the various stop and start sequences upon detection of a defect.

This controller (20) is connected to a keyboard (21), arranged on the console of the cloth examining machine within the operator's reach. This keyboard (21), upon detection of a defect, makes it possible to indicate the type of defect it is. These items of information are forwarded to the controller (20) which is in communication with a microcomputer (22) responsible for storing in memory the defects observed.

In order to locate the defects, the system for driving the drive rollers (9, 10) is associated with a coding wheel (23) driven by one of the drive rollers (10). The information delivered by this coder is delivered to the controller (20), so that it determines the prospective length to be wound on. This information is also forwarded to the microcomputer (22), so that the latter associates with the type of defect identified its exact location on the running web of cloth (1). Consequently, the set of data relating to the defect may be stored subsequent to use, printed, or displayed in real time.

The microcomputer (22) is also connected to a conventional laser sighting system (25) known per so, making it possible to determine the width of cloth inspected, so as to avoid possible variations therein.

As already mentioned, the invention consists in freeing the operator of the fastidious task of detecting the defects while at the same time enabling him to concentrate his attention on the fitting tasks of interpreting the defects detected.

For this purpose, according to the invention, the cloth examining machine comprises means for automatically detecting the defects. These means essentially consist of a camera (30), an illumination header (31), an electronic central processing unit (32), an additional coding wheel (33) and a polished plate (34) lying on the inclined plane (8) on the wrong side of the cloth.

The illumination header (31) makes it possible to obtain a line (36) of light arranged so as to be perpendicular to the run direction of the cloth, in the top part of the cloth examining table (8). This line (36) must be as bright as possible so as to allow detection of all types of defects. In order to take account of the various surface finishes of the cloth and of the weaving design, this illumination header (31) can be positionally adjusted with respect to the table and therefore with respect to the cloth. Thus, it is possible to adjust the distance of the header (31) from the table (8) by moving it in a particular direction with respect to said table. Moreover, it is also possible to adjust the angle of incidence of the light line (36) by rotating said header (31) about an axis parallel to the running plane and perpendicular to the run direction. Finally, in order to take account of the various mechanical tolerances, it is also possible to modify the inclination of the header (31) by making it pivot about an axis parallel to the run direction. In this way, it is possible to move one side end of the header closer while moving the opposite end of said header away from the cloth.

Figure 3:
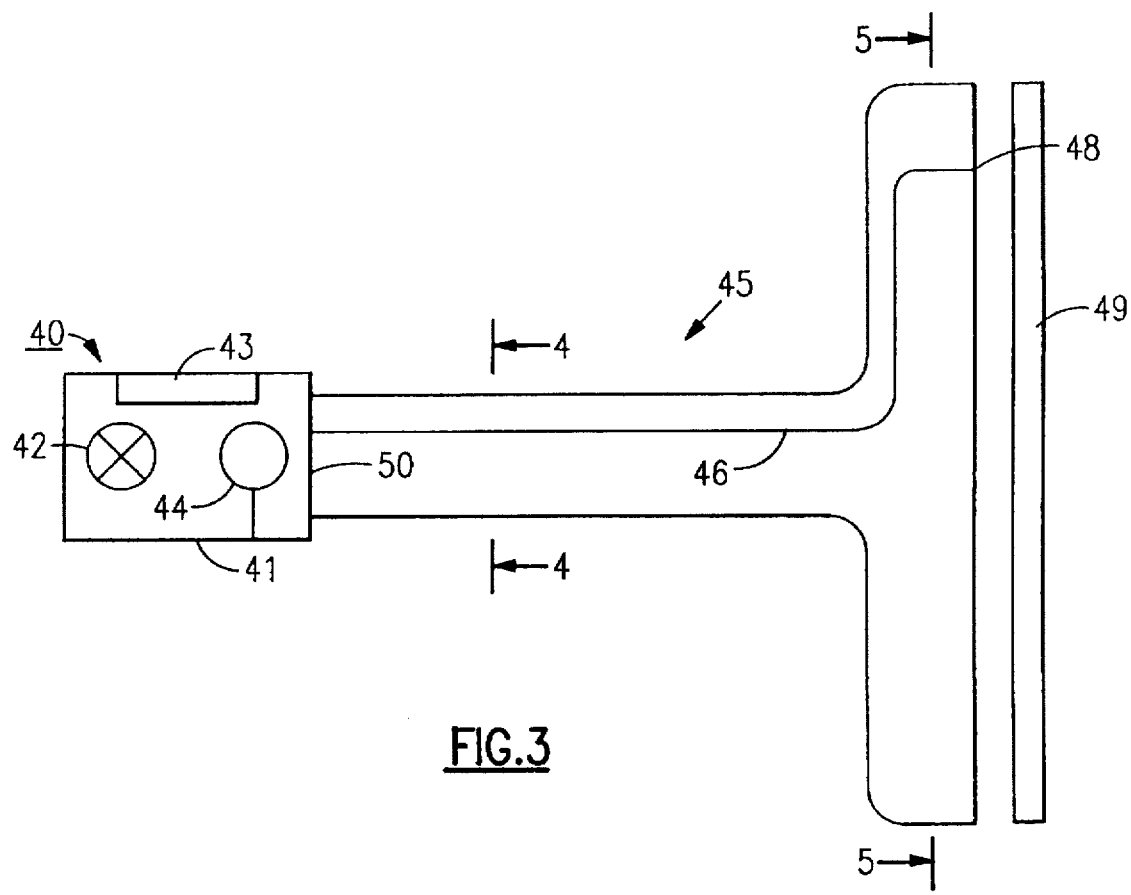
FIG. 3 is a side view of an individual assembly forming part of the illumination header.
Figure 4:
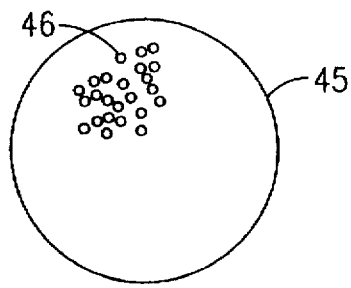
FIG. 4 is a section along the arrows IV—IV in FIG. 3 of the bundle of optical fibers in its concentrated part.
Figure 5:
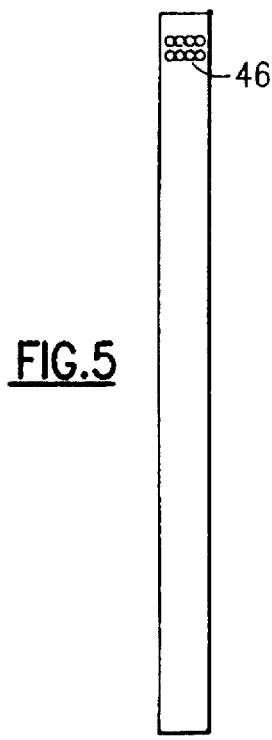
FIG. 5 is a sectional view along the arrows V—V in FIG. 3 of the bundle of optical fibers in its spread-out terminal part.

Each individual header (31) (see FIG. 3), is composed of a light source (40) which contains, in a housing (41), a halogen lamp having a typical power of one hundred and fifty watts and a fan-type cooling means (43).

This housing is connected to a bundle (45) of optical fibers. In order to avoid degradation, on account of the light power involved, of the cement forming the end (50) of the bundle (45), a heat-absorbing filter (44) is inserted between the lamp (42) and said bundle.

The bundle comprises several tens of thousands of parallel optical fibers combined together in a concentrated manner in the form of a cylinder in the distal region connected to the light source (40).

As has been shown, one of the main characteristics of the invention is the formation of a line (36) of light by means of the light header (31). For this purpose, the terminal end of the bundle is opened out and moved apart so as to form as straight an assembly as possible. The thousands of optical fibers, having a typical diameter of 50 microns, are distributed along a straight line in order substantially to form a rectangle having, for example, a short side of 300 microns and a length of 200 millimeters, consisting in its width direction of about four to six superimposed individual optical fibers. The header consists of a number of juxtaposed bundles described hereinabove. In order to avoid the light being concentrated in specific areas of each of the bundles, the various individual fibers making up each bundle are mixed up in order to ensure random distribution of the light paths. The light power dissipated by the light source (40) is put into the form of a line (36) by means of the characteristic bundle of optical fibers.

Figure 6:
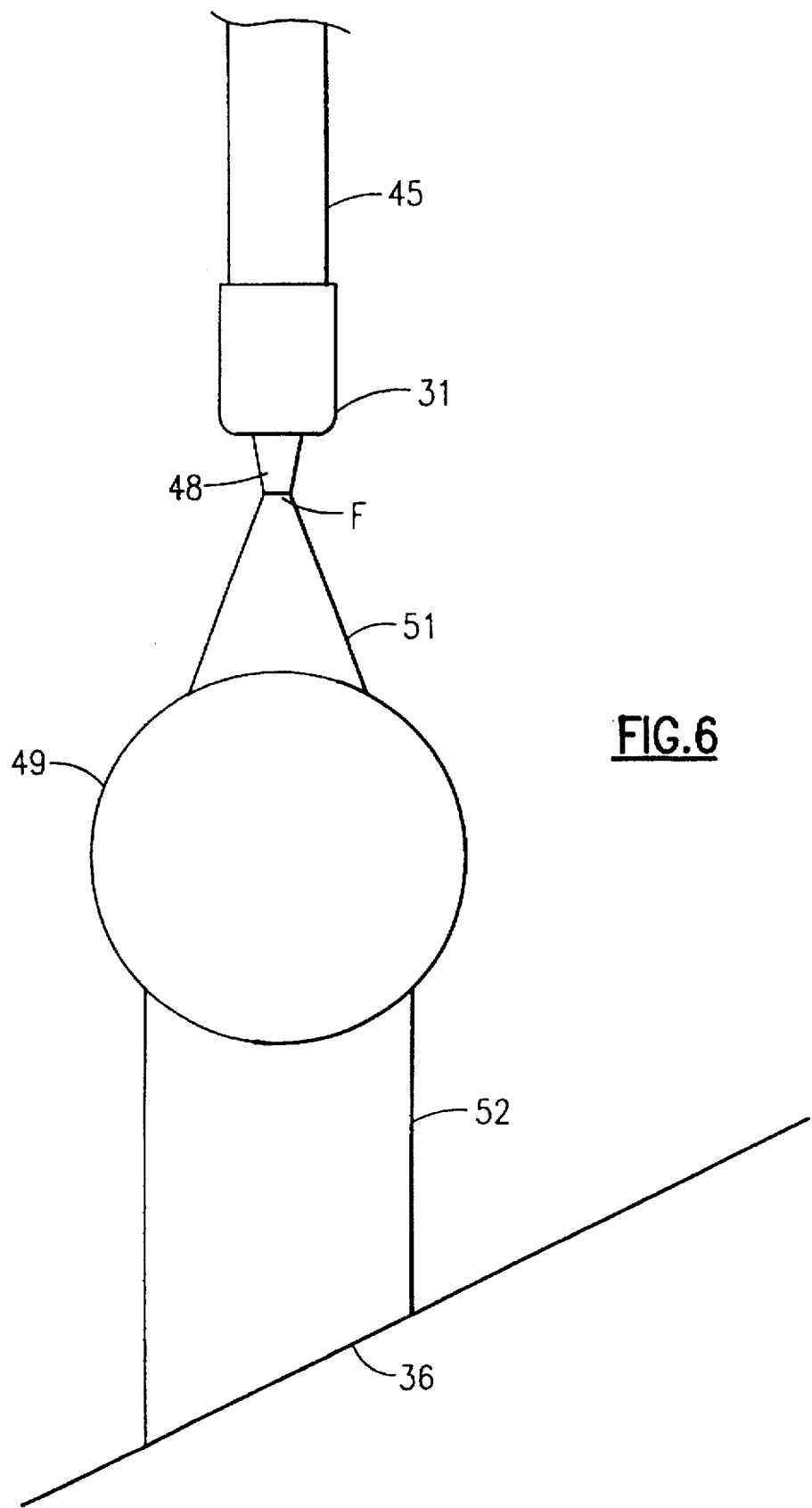
FIG. 6 is a detailed section of the end of the optical fibers and of the characteristic bar showing the path of the light lines.

In accordance with an essential characteristic of the invention, the fiber-optic header (31), in order to improve the focusing of the line of light, has a bar (49) capable of generating a beam of parallel lines, directed onto the cloth to be inspected. More specifically, as may be seen in FIG. 6, this bar is positioned in such a way that the object focal point (F) coincides exactly with the end (48) of the optical fibers. In this way, the light lines (51) emanating from the optical fibers (48), which diverge naturally, are deflected in such a manner as to form a parallel beam (52) pointed at the cloth. By virtue of this parallel beam, the device is insensitive to the exact distance separating the cloth to be inspected from the illumination assembly. Thus, this distance is determined in a sufficient manner to allow the operations of manually placing the cloth, without having to move away the illumination header or dismantle it.

This header (31) is present over the entire width of the cloth. It is produced from individual headers having a width of approximately twenty centimeters. Thus, for a typical cloth one meter sixty in width, it is necessary to combine together eight individual headers.

The line of light thus obtained is observed by a likewise characteristic camera (30). This camera (30) comprises a conventional objective system and includes a linear photosensitive detector (58) at its image focus. This linear photosensitive detector is a linear array having 2048 pixels along its length, each pixel typically being a square of 14 micrometers a side. Thus, and depending on the optical ratio of the objectives, this linear array observes a unitary width of the running cloth (1). Concomitantly, still depending on the ratio of the objectives, this linear array is capable of measuring a length "1" of the cloth in its run direction. As the cloth runs along, and each time a unitary individual length "1" is covered, the camera "30" captures an image and puts it at the disposal of the central processing unit (32). The linear array of photosensitive sensors may be replaced by a matrix sensor.

Detection of the cloth running along said length "1" is provided by means of the presence of an additional coding wheel (33), similar to (23), associated with the deflection roller (7). This coding wheel (33), the coding pitch of which is, of course, less than the characteristic distance "1", is connected to an acquisition card (56) of the central processing unit (32).

Depending on the running information delivered by the coding wheel (33), this acquisition card (56) sends the commands for triggering the camera (30).

Figure 7:
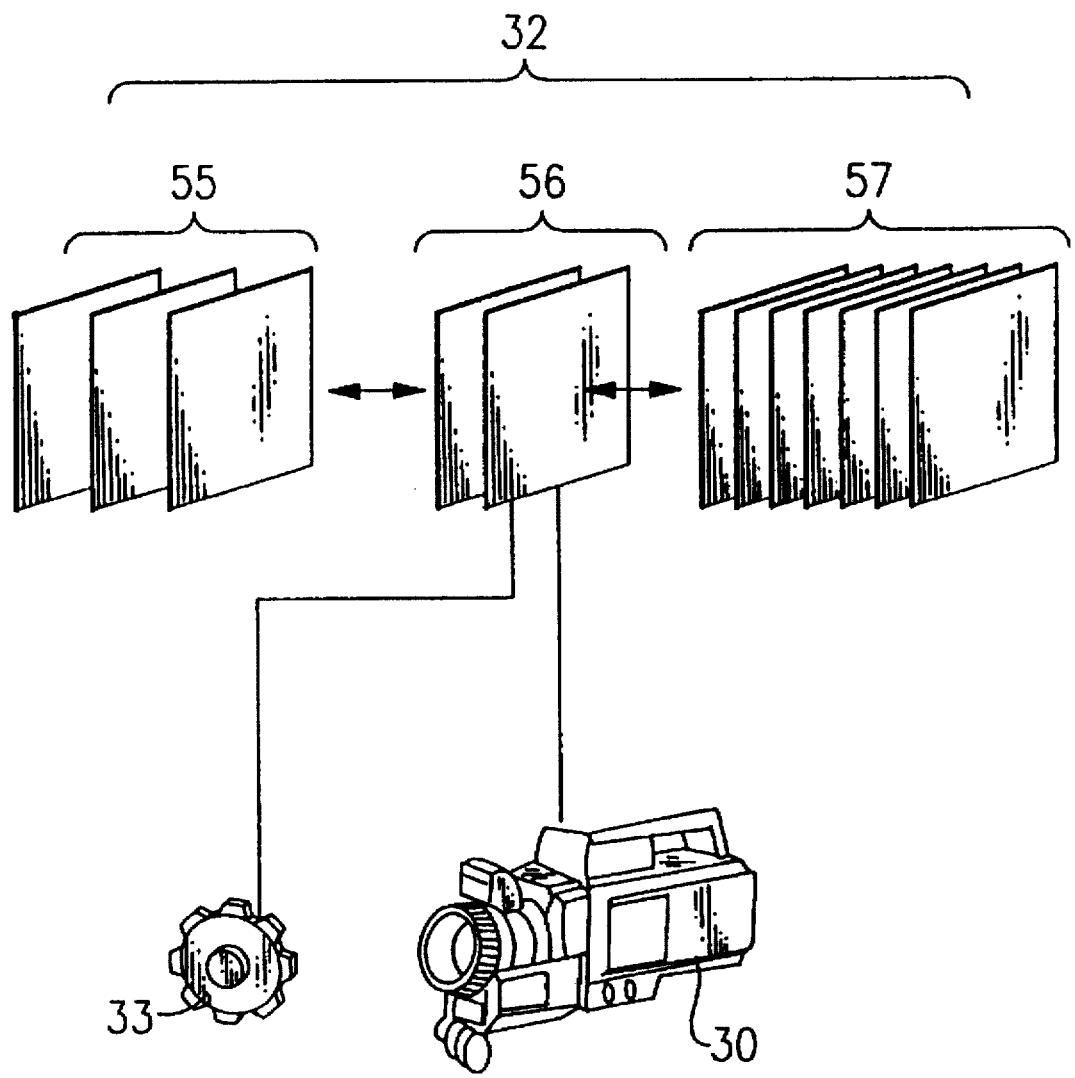
FIG. 7 is a general synoptical diagram of the central processing unit.

At the same time, the electronic system (32), (see FIG. 7), which conventionally comprises interface cards (55), acquisition cards (56) and a subassembly of parallel-processing cards (57), analyzes the images transmitted by the camera in accordance with processing algorithms which make it possible to detect the presence of an irregularity or a defect on the running cloth. Furthermore, the entire processing operation employs algorithms for determining the contrast of the images obtained, making it possible, during a learning phase, to determine and adjust the illuminating power of the light sources depending on the quality of the fabric. Thus, for example, it may be advantageous to illuminate a darkcolored plain cloth more strongly than a more reflecting light-colored cloth. This calibration makes it possible to avoid saturating the photosensitive sensors. Furthermore, as the illuminating lamps wear out, it may be advantageous to increase the light intensity.

Advantageously, the image processing system includes a plurality (57) of microprocessor cards in parallel, thereby, of course, increasing the processing speed.

In summary, the operation of the device is as follows. With the cloth (1) running, the coding wheel (33) continually communicates the information regarding the unreeled length to the central processing unit which commands the camera to carry out the sequenced triggering steps. After processing the images transmitted by the camera (30), the central processing unit (32), in the event of a defect being detected, commands the programmable controller (20) to carry out a stop sequence. At that moment, the cloth (1) having stopped, the operator interprets the defect observed and codes the type of defect on the keyboard (21). This information is then transmitted to the microcomputer (22) which stores it in memory, associating it with the position of the defect along the total length of the cloth, by virtue of the coder (23).

From the foregoing it is apparent that the cloth examining device in accordance with the invention has notable advantages, in particular:

the substantial increase in run speed, aiming at a speed of sixty to eighty or even 100 meters per minute;

moreover, it makes it possible to eliminate operator fatigue, the operator henceforth focusing his attention, strictly speaking, only on the fitting tasks of interpretation;

the use of optical fibers does not cause any degradation in the cloth, especially during the phase of stopping it running, since the optical fibers are a source of cold light;

the use of a concentrating bar makes it possible to decrease the illumination power and therefore to increase the lifetime of the lamps;

finally, it makes it possible to achieve inspection constancy as well as an increase in the proportion of defects identified since it is estimated that only 50% of these defects are detected using human vision, whereas more than 80% of the defects are detected by means of the automatic vision system according to the invention.

I claim:

1. Inspection apparatus for detecting defects on a running web of material that includes, drive means for drawing a web of material through an inspection zone, a header means containing a light transmitting fiber bundle having a light entrance face and a linear light exit face that extends across the width of the inspection zone, a light source for illuminating the light entrance face of said bundle whereby a line of illumination passes out of said bundle, a cylindrical transparent bar positioned in said line of illumination having a back focal point that coincides with the light exit face of the fiber bundle, whereby said line of illumination forms a parallel beam of light upon the web of material passing through said inspection zone, an array of photodetectors for detecting a reflected light image from the web passing through the inspection zone and generating a defect signal in response to the detected image, and means for storing in memory the position of a detected defect on said web.

2. The apparatus of claim 1 that further includes adjusting means for selectively positioning said header in reference to said web.

3. The apparatus of claim 2 wherein said adjusting means further includes an electrical control system for adjusting the distance between the header and the web, and the angle of inclination of the header.

4. The apparatus of claim 1 wherein the light source is a stabilized halogen lamp and contains a heat absorbing filter.

5. The apparatus of claim 1 that further includes a camera containing said photodetectors and a coder slaved to the camera to trigger said camera each time the web has advanced a given distance.

6. The apparatus of claim 5 wherein the coder has a coding pitch that is less than the length of the illuminated web that is detected by said photodetectors.

7. The apparatus of claim 1 wherein the inspection zone includes a light reflecting polished bar located on the back side of the web being drawn through said inspection zone to reflect that part of the light beam that has passed through the running web back to the photodetectors.

8. The apparatus of claim 1 that further includes a second light source to illuminate the backside of the web passing through the inspection zone.

9. The apparatus of claim 8 wherein the second light source contains a second header means.

10. The apparatus of claim 1 that further includes means for adjusting the intensity of the light source.

* * * * *